United States Patent

Araki et al.

[11] Patent Number: 5,945,420
[45] Date of Patent: Aug. 31, 1999

[54] IMMUNOPOTENTIATING AND INFECTION PROTECTIVE AGENT AND PRODUCTION THEREOF

[75] Inventors: Seiichi Araki; Mamoru Suzuki; Masatoshi Fujimoto, all of Ibaraki Prefecture, Japan

[73] Assignee: Eisai Co., Ltd., Japan

[21] Appl. No.: 09/060,329

[22] Filed: Apr. 15, 1998

Related U.S. Application Data

[62] Division of application No. 08/420,632, Apr. 12, 1995, Pat. No. 5,814,632, which is a division of application No. 08/204,333, filed as application No. PCT/JP92/01146, Sep. 9, 1992, abandoned.

[30] Foreign Application Priority Data

Sep. 13, 1991 [JP] Japan ................................ 3-261288

[51] Int. Cl.⁶ .................... A61K 31/525; A61K 31/685; A61K 31/65; A61K 31/43
[52] U.S. Cl. ........................... 514/251; 514/78; 514/152; 514/192; 514/315; 514/631
[58] Field of Search ................ 514/251, 78, 315, 514/631, 192, 152

[56] References Cited

U.S. PATENT DOCUMENTS

| | | | |
|---|---|---|---|
| 4,619,829 | 10/1986 | Motschan | 424/128 |
| 4,708,952 | 11/1987 | Salatinjants | 514/158 |
| 4,871,550 | 10/1989 | Millman | 424/601 |
| 5,290,571 | 3/1994 | Bounous et al. | 424/535 |

FOREIGN PATENT DOCUMENTS 0546870 6/1993 European Pat. Off. .

OTHER PUBLICATIONS

Windholz et al., *The Merck Index*, 10th Ed. p. 83, abstract No. 600 (1983).

*The Merck Index*, 10th Ed., Windholz et al., eds., abstract Nos. 8099 and 8100 (1983).

W. Serfontein, "Composition for treating obstructive air passages—comprises xanthine bronchodilator" (1991).

*Primary Examiner*—Kevin E. Weddington
*Attorney, Agent, or Firm*—Wenderoth, Lind & Ponack, L.L.P.

[57] ABSTRACT

An immunopotentiating and infection protective agent comprising riboflavin and/or a riboflavin derivative, which is safe for the human, animals or the like, an immunopotentiating and infection protective agent comprising riboflavin and/or a riboflavin derivative and (1) proline and/or glutamine, (2) an antibiotic, or (3) a water-soluble polymer or lecithin, which is safe for the human, animals or the like, and a process for the production thereof.

8 Claims, No Drawings

IMMUNOPOTENTIATING AND INFECTION PROTECTIVE AGENT AND PRODUCTION THEREOF

This is a divisional of Ser. No. 08/420,632, filed Apr. 12, 1995, U.S. Pat. No. 5,814,632 which is a divisional application of Ser. No. 08/204,333, filed Mar. 14, 1994, now abandoned which is a 371 of PCT/JP92/01146, filed Sep. 9, 1992.

INDUSTRIALLY APPLICABLE FIELD

The present invention relates to medicines for potentiating the immune function of the human, animals or the like so as to protect them from infection,, and a process for the production thereof.

PRIOR ART AND BACKGROUND OF THE INVENTION

Owing to the recent advancement of immunology, various disorders or infectious diseases of the human and animals have come to be considered to be caused by reduction or failure in immune function.

In the case of the human, for example, immune function is reduced or brought to failure by bronchial asthma, allergic diseases, articular rheumatism, autoimmune diseases, nutritional disorders, surgical operations, advanced age, pregnancy, etc. in many cases, so that infectious diseases such as respiratory infection, sepsis and urinary tract infection are developed at the same time. Various kinds of antibiotics have heretofore been administered against these disorders and infectious diseases.

In livestock and marine products industries on the other hand, large-scale operation or overcrowded breeding has been conducted in order to rear livestock, poultry or cultured fishes with high efficiency. The massive administration of antibiotics have been adopted in such breeding.

Under such circumstances, Japanese Patent Application Laid-Open (KOKAI) No. 286923/1987 discloses the fact that proline (pyrrolidine-2-carboxylic acid), which is a sort of amino acid produced by the decomposition of a protein, has an immune-enhancing action. Further, Japanese Patent Publication No. 38985/1988 discloses the fact that glutamine, which is a derivative of proline, has an immune-enhancing action.

Riboflavin useful in the practice of the present invention is phosphorylated in vivo to form twenty-odd flavoenzymes such as amino acid oxidases and xanthine oxidases as coenzymes (for example, flavin mononucleotide and flavin adenine dinucleotide), so that it participates in the oxidation-reduction mechanism of organism and plays an important part in metabolism of carbohydrates, lipids, proteins, etc.

In the case of humans, it is known that the lack of riboflavin leads to cheilitis, acute chronic eczema, solar eczema, seborrheic eczema, conjunctivitis, angular cheilitis, glossitis, pellagra or the like. Accordingly, riboflavin is used for preventing and treating these deficiency diseases of vitamine $B_2$.

Derivatives of riboflavin have been known to have substantially the same pharmacological action as that of riboflavin and to be applied to the same disorders or diseases.

Themes to be solved by the Invention:

When a specific antibiotic is used continuously, its resistant bacteria generates and the efficacy of the. antibiotic is lowered. Further, there is also a problem of nosocomial infection recently highlighted. Therefore, there is a demand for the development of a prophylactic and therapeutic drug which permits reduction in the amount of antibiotics to be used and can enhance immune function.

In the overcrowded breeding in the livestock and marine products industries on the other hand, there is a problem that various infectious diseases often develop due to stress and immunodeficiency in juvenile years. The massive administration of antibiotics as its countermeasure is accompanied this time by problems of retention of the antibiotics and increase of resistant bacteria.

In view of the above-described problems involved in antibiotics, the present inventors have carried out an extensive investigation for a long time with a view toward developing a infection protective agent safe for humans or animals. As a result, it has been found that riboflavin and/or riboflavin derivatives have an action to potentiate immune function, and also that water-soluble polymers and the like have an action to enhance and sustain the immune-function-potentiating action of riboflavin and/or the riboflavin derivatives, leading to completion of the present invention.

Means for Solving the Themes:

The present invention relates to an immunopotentiating and infection protective agent comprising riboflavin and/or a riboflavin derivative.

As described above, proline and glutamine have an action to potentiate immune function. However, it has been unexpectedly found that the combined use of riboflavin and/or the riboflavin derivative with proline and/or glutamine according to the present invention synergistically enhances the action to potentiate immune function. Therefore, the present invention relates to an immunopotentiating and infection protective agent comprising riboflavin and/or a riboflavin derivative and proline and/or glutamine.

It has been unexpectedly found that the combined use of riboflavin and/or a riboflavin derivative and an antibiotic develops a so-called synergism over those achieved by their single use. As a result, such combined use gives an important effect that the amount of the antibiotic to be used is decreased to a significant extent. Thus, the present invention relates to an immunopotentiating and infection protective agent comprising riboflavin and/or a riboflavin derivative and an antibiotic.

Further, it has been unexpectedly found that the combined use of riboflavin and/or a riboflavin derivative and a water-soluble polymer or lecithin enhance the infection protective effect of riboflavin and/or the riboflavin derivative. Therefore, the present invention relates to an immunopotentiating and infection protective agent comprising riboflavin and/or a riboflavin derivative and a water-soluble polymer or lecithin.

Further, it has been unexpectedly found that the combined use of riboflavin and/or a riboflavin derivative and a vaccine exhibits a so-called synergism over the immunopotentiating and infection protective effects achieved by their single use. Thus, the present invention relates to a vaccine preparation comprising riboflavin and/or a riboflavin derivative and a vaccine.

The present invention is also concerned with a process for the production of an immunopotentiating and infection protective agent comprising riboflavin and/or a riboflavin derivative and a water-soluble polymer or lecithin.

The immunopotentiating and infection protective agent comprising riboflavin and/or a riboflavin derivative and lecithin, or the immunopotentiating and infection protective agent comprising riboflavin and/or a riboflavin derivative and a water-soluble polymer can not be prepared by simple mixing because parts of riboflavin derivatives and lecithins are hard to dissolve in water. Such an agent can be prepared by emulsifying the riboflavin derivative or lecithin. Therefore, the present invention is also related to a process for the production of an immunopotentiating and infection protective agent, which comprises emulsifying lecithin and riboflavin and/or a riboflavin derivative in a solvent, or emulsifying riboflavin and/or a riboflavin derivative and a water-soluble polymer in a solvent.

It is an object of the present invention to provide an agent which can potentiate immune function and is safe for the human or animals without the above-described drawbacks involved in the administration of antibiotics, thereby permitting the protection of an organism from infection, and a process for the production thereof.

The term "immunopotentiating" as used herein means enhancing immune function in the human, animals, for example, fish, or the like.

Therefore, since the immunopotentiating and infection protective agents according to the present invention are useful as agents for enhancing the immune function of the human, animals or the like so as to prevent and treat various disorders and infectious diseases, no particular limitation is imposed on their cases to be applied. In the case of the human, they are applied to, for example, cancers, organ transplantations, leukopenia, articular rheumatism, autoimmune diseases, bronchial asthma, nutritional disorders, surgical operations, age diseases and various infectious diseases such as respiratory infection, sepsis and urinary tract infection.

In the case of the animals, they are applied to, for example, the diarrhea, epidemic pneumonia, atrophic rhinitis, infectious gastroenteritis and the like of swine, the pneumonia and Marek's disease of domestic fowl, the diarrhea, pneumonia and udder inflammation of bovine, the AIDS of pets and the leukemia of cats.

Further, no particular limitation is imposed on infectious diseases of cultured fishes, to which the immunopotentiating and infection protective agents according to the present invention are applied. However, they are used widely for bacterial infections such as streptococcosis and pseudotuberculosis, virus infections, and the like.

In the present invention, riboflavin and the riboflavin derivative may be used either singly or in combination. Examples of the riboflavin derivative include flavin mononucleotide, flavin adenine nucleotide and pharmacologically permissible salts of riboflavin (for example, sodium riboflavin phosphate, the monodiethanolamine salt of riboflavin phosphate, etc.).

No particular limitation is imposed on the amount of riboflavin and/or the riboflavin derivative to be used in the present invention because it varies according to the species of animal to be applied, and the like. In general, its dose falls within a range of 0.1–500 mg/kg of weight, preferably 1–100 mg/kg of weight.

No particular limitation is imposed on the compounding ratio of riboflavin and/or the riboflavin derivative to proline and/or glutamine in the present invention. However, the compounding ratio of proline and/or glutamine is generally 0.1–10 parts by weight, preferably 0.5–5 parts by weight based on 1 part by weight of riboflavin and/or the riboflavin derivative.

In the present invention, proline and glutamine may be incorporated singly into riboflavin and/or the riboflavin derivative. Alternatively, a mixture of both proline and glutamine may be incorporated into riboflavin and/or the riboflavin derivative.

Further, no particular limitation is imposed on the kind of the antibiotic used in combination with riboflavin and/or the riboflavin derivative. However, amoxicillin, tetracycline, oxycycline hydrochloride may be mentioned by way of example.

Amoxicillin is a penicillin antibiotic, has an antibacterial action owing to the inhibition of cell wall synthesis, and is applied to various infectious diseases caused by *Escherichia coli, Haemophilus influenzae,* haemolytic streptococcus, staphylococcus and the like, which are sensitive to amoxicillin.

Further, no particular limitation is imposed on the compounding ratio of riboflavin and/or the riboflavin derivative to the antibiotic in the present invention. However, the compounding ratio of the antibiotic is generally 0.01–1 part by weight, preferably 0.05–0.5 part by weight based on 1 part by weight of riboflavin and/or the riboflavin derivative.

Further, no particular limitation is imposed on the compounding ratio of riboflavin and/or the riboflavin derivative to the water-soluble polymer or lecithin in the present invention. However, the compounding ration of the water-soluble polymer or lecithin is generally 0.01–100 parts by weight, preferably 0.05–50 parts by weight, more preferably 0.1–10 parts by weight based on 1 part by weight of riboflavin and/or the riboflavin derivative.

No particular limitation is imposed on the water-soluble polymer. However, preferred water-soluble polymers include polyvinyl pyrrolidone, sodium carboxymethyl cellulose, methyl cellulose, hydroxypropyl cellulose, hydroxypropylmethyl cellulose, sodium chondroitin sulfate, polyethylene-hardened castor oil, polyoxysorbitan fatty acid esters and polyvinyl alcohol. These polymers may be used singly or in any combination thereof.

No particular limitation is imposed on the lecithin. However, yolk lecithin, soybean lecithin and hydrogenated lecithins thereof may be mentioned and used in a single form or in any combination thereof.

Further, no particular limitation is imposed on the kind and compounding ratio of the vaccine to be used in combination with riboflavin and/or the riboflavin derivative in the present invention because they vary according to the species to be applied, such as the human or animals, e g., fish. However, examples of such a vaccine include various kinds of vaccines such as a chicken mycoplasma vaccine, chicken infectious coryza type A.C inactivated vaccine, swine Bordetella inactivated vaccine and swine Haernophilus (Actinobacillus) inactivated vaccine in the case of the animals.

No particular limitation is imposed on the form of the immunopatentiating and infection protective agent according to the present invention when it is administered to the human or an animal. However, it may be formed into an injection, granules, powder, tablets, or the like.

When the immunopotentiating and infection protective agent according to the present invention is prepared, various kinds of additives may be incorporated according to the form prepared. For example, an excipient, colorant, lubricant, binder, coating and the like may be incorporated when prepared in the form of a solid or powder.

When low-solubility substances are prepared in injections, a dissolution aid such as a surfactant is often used. In the present invention, a surfactant such as polyoxyethylene-hardened castor oil, or the like is also used. These substances are added on the basis of an unexpected finding that they can enhance the immunopotentiating and infection protective action of riboflavin and/or the riboflavin derivative, and hence do not have a mere effect as a dissolution aid.

The immunopotentiating and infection protective agent according to the present invention, which comprises riboflavin and/or the riboflavin derivative, or proline and/or glutamine in addition to riboflavin and/or the riboflavin derivative, may be added to food so as to use it as a food specifically intended for the prevention of individual diseases or disorders and having a biological control function, i.e., a so-called functional food.

Further, since the immunopotentiating and infection protective agent according to the present invention is free of the influence of resistant bacteria and the problem of retention, which are recognized in antibiotics, it may be used for livestock such as swine, domestic fowl, bovine, equine and ovine, fish, pets (dogs, cats, birds), and the like as a safe feed having a biophylatic control function, i.e., a functional feed.

The immunopotentiating and infection protective agent according to the present invention, which comprises riboflavin and/or the riboflavin derivative, or an antibiotic in addition to riboflavin and/or the riboflavin derivative, is administered in the form of intramuscular injection, intravenous injection, subcutaneous injection or oral administration when given to the human or animals.

Function:

The present inventors do not completely elucidate the mechanism of intravital action in which the riboflavin derivatives potentiate immune function. However, it has been recognized that the riboflavin derivatives activate phagocytes, for example, macrophages, in leukocytes and neutrophiles. In addition, it has also been found that the number of leukocytes (in particular, the number of neutrophiles, and the like) is increased.

EXAMPLES

The present invention will hereinafter be described specifically by the following examples. In the following examples, the description on the doses of substances to be used, for example, "110 mg/kg i.m." means that intramuscular injection was conducted in a proportion of 10 mg per kg of weight. Further, the designations of "*" and "**" as will be used in the column of $x^2$-test in Tables 1 to 7 mean p<0.05 and p<0.01, respectively.

Example 1

Riboflavin in proportions of 10, 30 and 100 mg/kg and physiological saline as a control were intramuscularly injected into each 10 SLC:ICR male mice (aged 5–6 weeks, weight: 25–30 g). After 24 hours, clinically derived *Escherichia coli* ($2.6\times10^7$ CFU/mouse, 0.2 ml) was subcutaneously inoculated into the mice in each group to determine the survival rate from the viable count on the 7th day from the infection, thereby finding the significance to the control. The results are shown in Table 1.

TABLE 1

| Sample | Survival rate % | $x^2$-Test |
| --- | --- | --- |
| Control (physiological saline, i.m.) | 10 | |
| Riboflavin, 10 mg/kg i.m. | 20 | |
| Riboflavin, 30 mg/kg i.m. | 50 | |

TABLE 1-continued

| Sample | Survival rate % | $x^2$-Test |
| --- | --- | --- |
| Riboflavin, 100 mg/kg i.m. | 90 | ** |

As shown in Table 1, the effect of riboflavin increases in dependence on the doses. It is therefore apparent that riboflavin has an infection protective effect. The effect of riboflavin is powerful as demonstrated by the survival rates of 50% and 90% in doses of 30 mg/kg and 100 mg/kg, respectively.

Example 2

Glutamine, proline and riboflavin, and a control (physiological saline) were intramuscularly injected into each 10 SLC:ICR male mice (aged 5–6 weeks, weight: 22–30 g) either singly or in combination with each other as shown in Table 2. After 24 hours, clinically derived *Escherichia coli* ($2.6\times10^7$ CFU/mouse, 0.2 ml) was inoculated into the mice in each group to determine the survival rate from the viable count on the 7th day from the infection.

With respect to sole glutamine, proline or riboflavin and their combinations with each other, the significance was found to the control. The results are shown in Table 2.

TABLE 2

| Sample | Survival rate % | $x^2$-Test |
| --- | --- | --- |
| Control (physiological saline, i.m.) | 0 | |
| Glutamine, 100 mg/kg i.m. | 30 | |
| Proline, 100 mg/kg i.m. | 40 | * |
| Glutamine, 100 mg/kg;<br>Proline, 100 mg/kg i.m. | 50 | * |
| Riboflavin, 10 mg/kg i.m. | 20 | |
| Riboflavin, 30 mg/kg i.m. | 50 | * |
| Riboflavin, 100 mg/kg i.m. | 90 | ** |
| Glutamine, 100 mg/kg;<br>Proline, 100 mg/kg;<br>Riboflavin, 10 mg/kg i.m. | 100 | ** |

Further, with respect to the combination of glutamine, proline and riboflavin, the significance was found to the combination of glutamine and proline. The results are shown in Table 3.

TABLE 3

| Sample | Survival rate % | $x^2$-Test |
| --- | --- | --- |
| Glutamine, 100 mg/kg;<br>Proline, 100 mg/kg i.m. | 50 | |
| Glutamine, 100 mg/kg;<br>Proline, 100 mg/kg;<br>Riboflavin, 10 mg/kg i.m. | 100 | * |

As shown in Table 2, the survival rate owing to proline in a dose of 100 mg/kg is 40% and proline is hence significant compared with the control. This indicates that proline has an infection protective effect. The survival rates owing to riboflavin in doses of 30 mg/kg and 100 mg/kg are 50% and 90%, respectively. It is understood that riboflavin exhibits a more powerful infection protective effect in dependence on its doses even when compared with proline.

It was confirmed from Table 2 that the combination of glutamine, proline and riboflavin has an effect more than the additive effect as the sum of effects achieved by using the respective components singly, i.e., a synergism.

In addition, it is also understood from Table 3 that the combination of glutamine, proline and riboflavin exhibits an infection protective effect as extremely powerful as 100% in survival rate. When compared with the additive effect of the effect in the combination of glutamine and proline and the effect in the single use of riboflavin, it was confirmed that the combination of the three components has a clearly significant synergism.

Example 3

Sodium riboflavin phosphate in proportions of 10, 30, 100 and 300 mg/kg and physiological saline as a control were intramuscularly injected into each 10 SLC:ICR male mice (aged 5–6 weeks, weight: 25–30 g). After 24 hours, clinically derived Escherichia coli ($2.6 \times 10^7$ CFU/mouse, 0.2 ml) was subcutaneously inoculated into the mice in each group to determine the survival rate from the viable count on the 7th day from the infection, thereby finding the significance to the control. The results are shown in Table 4.

TABLE 4

| Sample | Survival rate % | $x^2$-Test |
|---|---|---|
| Control (physiological saline, i.m.) | 0 | |
| Sodium riboflavin phosphate, 10 mg/kg i.m. | 10 | |
| Sodium riboflavin phosphate, 30 mg/kg i.m. | 40 | * |
| Sodium riboflavin phosphate, 100 mg/kg i.m. | 60 | ** |
| Sodium riboflavin phosphate, 300 mg/kg i.m. | 100 | ** |

As shown in Table 4, the effect of sodium riboflavin phosphate increases in dependence on the doses, i.e., 10, 30, 100 and 300 mg/kg. In particular, it was confirmed that the use of sodium riboflavin phosphate in a proportion of 300 mg/kg exhibits an extremely powerful infection protective effect.

Example 4

Sodium riboflavin phosphate and amoxicillin (AMPC) in proportions of 10 mg/kg and 0.39 mg/kg, respectively, were intramuscularly injected into each 10 SLC:ICR male mice (aged 5–6 weeks, weight: 25–30 g) either singly or in combination with each other 24 hours before infection and 30 minutes after infection. Clinically derived Escherichia coli ($2.6 \times 10^7$ CFU/mouse, 0.2 ml) was subcutaneously inoculated into the mice in each group to determine the survival rate from the viable count on the 7th day from the infection. The results are shown in Table 5.

TABLE 5

| Sample | Survival rate % | $x^2$-Test |
|---|---|---|
| Control (physiological saline, i.m.) | 0 | |
| Amoxicillin, 0.39 mg/kg i.m. | 60 | ** |
| Sodium riboflavin phosphate, 10 mg/kg i.m. | 10 | |
| Amoxicillin, 0.39 mg/kg; Sodium riboflavin phosphate, 10 mg/kg i.m. | 100 | ** |

As shown in Table 5, it was confirmed that the combination of amoxicillin and sodium riboflavin phosphate has an effect mote than the additive effect as the sum of effects achieved by using the respective components singly, i.e., a significant synergism.

Example 5 flavin mononucleotide (FMN) and riboflavin in proportions of 100 mg/kg, and polyvinyl pyrrolidone (PVP-K30), sodium carboxymethyl cellulose (CMC Na), purified soybean lecithin, yolk lecithin, polyoxyethylene (60) ether (HCO-60), polyoxyethylene (20) sorbitan monooleate (Tween-80) and a control (physiological saline) were intramuscularly injected into each 10 SLC:ICR ma e mice (aged 5–6 weeks, weight: 25–30 g) in combination with each other as shown in the following Table 6. After 3 days, clinically derived Escherichia coli ($2.6 \times 10^7$ CFU/mouse, 0.2 ml) was subcutaneously inoculated into the mice in each group to determine the survival rate from the viable count on the 7th day from the infection, thereby finding the significance to the control. The results are shown in Table 6.

TABLE 6

| Sample | Survival rate % | $x^2$-Test |
|---|---|---|
| Control (physiological saline, i.m.) | 0 | |
| FMN, 100 mg/kg i.m. | 30 | |
| FMN, 100 mg/kg; PVP-K30, 300 mg/kg i.m. | 40 | * |
| FMN, 100 mg/kg; CMC Na, 30 mg/kg i.m. | 50 | * |
| FMN, 100 mg/kg; Purified soybean lecithin, 200 mg/kg i.m. | 70 | ** |
| FMN, 100 mg/kg; Yolk lecithin, 100 mg/kg i.m. | 90 | ** |
| FMN, 100 mg/kg i.m.; HCO-60 10 mg/kg i.m. | 30 | |
| Riboflavin, 100 mg/kg i.m. | 40 | * |
| Riboflavin, 100 mg/kg; PVP-K30, 300 mg/kg i.m. | 90 | ** |
| Riboflavin, 100 mg/kg; CMC Na, 30 mg/kg i.m. | 80 | ** |
| Riboflavin, 100 mg/kg; Purified soybean lecithin, 200 mg/kg i.m. | 90 | ** |
| Riboflavin, 100 mg/kg; Yolk lecithin, 100 mg/kg i.m. | 100 | ** |
| Riboflavin, 100 mg/kg; HCO-60 10 mg/kg i.m. | 50 | * |
| Riboflavin, 100 mg/kg; Tween-80, 10 mg/kg i.m. | 70 | ** |

As shown in Table 6, it was confirmed that the various water-soluble polymers such as polyvinyl pyrrolidone (PVP-K30), sodium carboxymethyl cellulose (CMC Na), polyoxyethylene (60) ether (HCO-60) and polyoxyethylene (20) sorbitan monooleate (Tween-80), and lecithins such as purified soybean lecithin and yolk lecithin enhance and sustain the infection protective effect of FMN and riboflavin.

Example 6

Riboflavin or sodium riboflavin phosphate and yolk lecithin were used either singly or in combination with each other as shown in Table 7 to dilute them with a 20-fold phosphate buffer. Portions of the resulting dilute solutions were mixed with commercially-available Actinobacillus pleueopneumoniae inactivated vaccine to produce vaccine preparations. The thus-produced vaccine preparations, the residual dilute solutions and a phosphate buffer as a control in amounts of,0.5 ml were intraperitoneally administered into each 20 SLC:ICR male mice (aged 3 weeks, weight: 12–15 g). Upon elapsed time of 14 days after the administration, 0.5 ml of Actinobacillus pleueopneumoniae ($3 \times 10^8$ CFU/mouse) was intraperitoneally inoculated into the mice in each group to determine the survival rate after 7 days. The results are shown in Table 7. This experiment was carried out in accordance with the method of national certification of vaccine.

TABLE 7

| Sample | Survival rate % | $x^2$-Test |
| --- | --- | --- |
| Control (phosphate buffer, i.p.) | 10 | |
| Vaccine, i.p. | 40 | |
| Riboflavin, 100 mg/kg i.p. | 25 | |
| Riboflavin, 100 mg/kg; vaccine, i.p. | 80 | ** |
| Riboflavin, 100 mg/kg; Yolk lecithin, 100 mg/kg; Vaccine, i.p. | 95 | ** |
| Sodium riboflavin phosphate, 100 mg/kg i.p. | 5 | |
| Sodium riboflavin phosphate, 100 mg/kg; Vaccine, i.p. | 50 | |
| Sodium riboflavin phosphate, 100 mg/kg; Yolk lecithin, 100 mg/kg; Vaccine, i.p. | 60 | ** |

As shown in Table 7, it was confirmed that the combination of riboflavin or sodium riboflavin phosphate and the vaccine has an effect more than the additive effect as the sum of infection protective effects achieved by using the respective components singly, i.e., a significant synergism. This synergism means the enhanced infection protective effect of the vaccine, i.e., is nothing but the enhancement effect on the vaccine.

Example 7

Five grams of flavin mononucleotide (FMN), 5 g of D-sorbitol, 0.04 g of disodium phosphate, 0.04 g of monosodium phosphate and 15 g of polyvinyl pyrrolidone (PVP-K30) were dissolved in water for injection into 100 ml of a solution. The resulting solution was poured in parts into 5-ml ampules and sterilized with steam, thereby preparing immunopotentiating and infection protective agents.

Example 8

Immunopotentiating and infection protective agents were prepared in the same manner as in Example 7 except that 3 g of hydroxypropyl cellulose (HPC) was used in place of 15 g of PVP-K30 in Example 7.

Example 9

Immunopotentiating and infection protective agents were prepared in the same manner as in Example 7 except that of 2 g of hydroxypropylmethyl cellulose (HPMC) was used in place of 15 g of PVP-K30 in Example 7.

Example 10

Immunopotentiating and infection protective agents were prepared in the same manner as in Example 7 except that 20 g of sodium chondroitin sulfate was used in place of 15 g of PVP-K30 in Example 7.

Example 11

After 10 g of yolk lecithin was dispersed in an ultrasonic emulsifier, 5 g of D-sorbitol, 0.03 g of disodium phosphate, 0.02 g of monosodium phosphate and 3 g of FMN were dissolved in the resulting dispersion, followed by dissolution of the resulting solution in water for injection into 100 ml of another solution. The thus-obtained solution was poured in parts into 5-ml ampules and sterilized with steam, thereby preparing immunopotentiating and infection protective agents.

Example 12

Immunopotentiating and infection protective agents were prepared in the same manner as in Example 11 except that 10 g of partially hydrogenated soybean lecithin was used in place of 10 g of yolk lecithin in Example 11 and the amount of FMN was changed to 4 g.

Example 13

Five grams of microcrystalline riboflavin were suspended in water for injection, which contained 5 g of D-sorbitol, 1 g of sodium carboxymethyl cellulose (CMC Na), 0.04 g of disodium phosphate and 0.04 g of monosodium phosphate, into 100 ml of a suspension. This suspension was dispersed in an ultrasonic emulsifier. The resulting dispersion was poured in parts into 5-ml ampules and sterilized with steam, thereby preparing immunopotentiating and infection protective agents.

Example 14

Immunopotentiating and infection protective agents were prepared in the same manner as in Example 13 except that 3 g of HPMC was used in place of 1 g of CMC-NA in Example 13.

Example 15

Immunopotentiating and infection protective agents were prepared in the same manner as in Example 13 except that 3 g of polyvinyl alcohol was used in place of 1 g of CMC-NA in Example 13.

Example 16

After 10 g of partially hydrogenated yolk lecithin and 5 g of D-sorbitol were dispersed in an ultrasonic emulsifier, 0.03 g of disodium phosphate, 0.02 g of monosodium phosphate and 3 g of FMN were dissolved in the resulting dispersion. The resulting solution was added with 5 g of riboflavin to suspend it, followed by dissolution of the resulting suspension in water for injection into 100 ml of another solution. The thus-obtained solution was poured in parts into 5-ml ampules and sterilized with steam, thereby preparing immunopotentiating and infection protective agents.

The immunopotentiating and infection protective agents according to the present invention were prepared in accordance with the processes for the production described in Examples 7 to 16.

Effect of the Invention:

From the above Examples, the immunopotentiating and infection protective agents and vaccine preparations have an excellent immune-function-potentiating action. Therefore, they are useful as prophylactic and therapeutic drugs for various disorders and infectious diseases.

We claim:

1. A method for protection against infection which comprises administering to a patient in need of such protection a composition comprising riboflavin and/or a riboflavin derivative.

2. The method according to claim 1 wherein the riboflavin derivative is flavin mononucleotide, flavin adenine dinucleotide or a pharmacologically acceptable salt of riboflavin.

3. The method according to claim 1 wherein the composition comprises riboflavin and/or a riboflavin derivative and an antibiotic.

4. The method according to claim 1 wherein the composition is administered to the patient in an amount ranging from 0.1 to 500 mg/kg of weight of the patient.

5. The method according to claim 1 wherein the composition is administered to the patient in a form of intramuscular injection, intravenous injection, subcutaneous injection or oral administration.

6. A method for protection against infection which comprises administering to a patient in need of such protection a composition comprising riboflavin and/or a riboflavin and/or a riboflavin derivative and a water-soluble polymer or lecithin.

7. The method according to claim 6 wherein the water-soluble polymer is one or more selected from the group consisting of polyvinyl pyrrolidone, sodium carboxymethyl cellulose, methy cellulose, hydroxypropyl cellulose, hydroxypropylmethyl cellulose, sodium chondroitinn sulfate, polyethylene-hardened castor oil, polyoxysorbitan faty acid esters and polyvinlyl alcohol.

8. The method according to claim 6 wherein the lecithin is one or more selected from the group consisting of yolk lecithin, soybean lecithin and hydrogenated lecithins thereof.

* * * * *